(12) United States Patent
Wenz (10) Patent No.: US 8,168,692 B2
(45) Date of Patent: May 1, 2012

(54) BONE SUBSTITUTE COMPOSITIONS AND METHOD OF USE

(75) Inventor: Robert Wenz, Wollstadt (DE)

(73) Assignee: Kyphon SARL, Neuchatel (CH)

( * ) Notice: Subject to any disclaimer, the term of this patent is extended or adjusted under 35 U.S.C. 154(b) by 1352 days.

(21) Appl. No.: 11/116,656

(22) Filed: Apr. 27, 2005

(65) Prior Publication Data

US 2005/0251149 A1 Nov. 10, 2005

Related U.S. Application Data (60) Provisional application No. 60/565,986, filed on Apr. 27, 2004.

(51) Int. Cl.
*A61K 6/08* (2006.01)
(52) U.S. Cl. .......................... 523/116; 606/94
(58) Field of Classification Search .............. 606/92–94; 523/105, 113–118; 106/35; 623/23.51, 23.61, 623/23.62, 925, 926
See application file for complete search history.

(56) References Cited

U.S. PATENT DOCUMENTS

| | | |
|---|---|---|
| 3,746,680 A | 7/1973 | Boricheski |
| 4,141,864 A | 2/1979 | Rijke et al. |
| 4,192,021 A | 3/1980 | Deibig et al. |
| 4,239,113 A | 12/1980 | Gross et al. |
| 4,341,691 A | 7/1982 | Anuta |
| 4,404,327 A | 9/1983 | Crugola et al. |
| 4,518,430 A | 5/1985 | Brown et al. |
| 4,588,583 A | 5/1986 | Pietsch et al. |
| 4,612,053 A | 9/1986 | Brown et al. |
| 4,629,464 A | 12/1986 | Takata et al. |
| 4,678,436 A | 7/1987 | Kondo et al. |
| 4,722,948 A | 2/1988 | Sanderson |
| 4,791,150 A | 12/1988 | Braden et al. |
| 4,872,936 A | 10/1989 | Engelbrecht |
| 4,902,649 A | 2/1990 | Kimura et al. |
| 4,940,689 A | 7/1990 | Ito |
| 4,957,352 A | 9/1990 | Yasuda et al. |
| 4,959,104 A | 9/1990 | Iino et al. |
| 5,004,501 A | 4/1991 | Faccioli et al. |
| 5,108,956 A | 4/1992 | Inoue et al. |
| 5,149,368 A | 9/1992 | Liu et al. |
| 5,160,371 A | 11/1992 | Ito |
| 5,171,720 A | 12/1992 | Kawakami |
| 5,179,065 A | 1/1993 | Ito |
| 5,204,382 A * | 4/1993 | Wallace et al. ............ 523/115 |
| 5,205,928 A | 4/1993 | Inoue et al. |
| 5,226,877 A * | 7/1993 | Epstein ..................... 604/35 |

(Continued)

FOREIGN PATENT DOCUMENTS

DE 29607832 10/1996

(Continued)

OTHER PUBLICATIONS

Heini, P.F., et al., "Bone substitutes in vertebroplasty," *Eur. Spine J.*, Jun. 14, 2001, vol. 10, pp. S205-S213.

(Continued)

*Primary Examiner* — Eduardo C Robert
*Assistant Examiner* — Tara Carter (57) ABSTRACT

The present invention relates to novel bone substitute compositions and methods of use. It further encompasses the use of these novel bone substitute compositions for bone augmentation and the treatment of disease conditions. The invention also contemplates a kit including bone substitute compositions and a percutaneous delivery device.

23 Claims, 1 Drawing Sheet

U.S. PATENT DOCUMENTS

| | | | |
|---|---|---|---|
| 5,262,166 A | 11/1993 | Liu et al. | |
| 5,276,070 A | 1/1994 | Arroyo | |
| 5,281,265 A | 1/1994 | Liu | |
| 5,352,715 A | 10/1994 | Wallace et al. | |
| 5,462,356 A | 10/1995 | Murray | |
| 5,462,722 A * | 10/1995 | Liu et al. | 423/311 |
| 5,522,893 A | 6/1996 | Chow et al. | |
| 5,545,254 A | 8/1996 | Chow et al. | |
| 5,605,713 A | 2/1997 | Boltong | |
| 5,650,108 A | 7/1997 | Nies et al. | |
| 5,695,729 A | 12/1997 | Chow et al. | |
| 5,795,922 A * | 8/1998 | Demian et al. | 523/117 |
| 5,797,873 A | 8/1998 | Franz et al. | |
| 5,814,683 A | 9/1998 | Branham | |
| 5,847,046 A | 12/1998 | Jiang et al. | |
| 5,914,356 A | 6/1999 | Erbe | |
| 5,952,010 A | 9/1999 | Constantz | |
| 6,002,065 A * | 12/1999 | Constantz et al. | 423/308 |
| 6,075,067 A | 6/2000 | Lidgren | |
| 6,124,373 A | 9/2000 | Peter et al. | |
| 6,153,664 A | 11/2000 | Wise et al. | |
| 6,187,046 B1 | 2/2001 | Yamamoto et al. | |
| 6,203,574 B1 | 3/2001 | Kawamura | |
| 6,206,957 B1 | 3/2001 | Driessens et al. | |
| 6,224,635 B1 | 5/2001 | Ricci et al. | |
| 6,231,615 B1 | 5/2001 | Preissman | |
| 6,241,734 B1 | 6/2001 | Scribner et al. | |
| 6,248,110 B1 * | 6/2001 | Reiley et al. | 606/93 |
| 6,273,916 B1 | 8/2001 | Murphy | |
| 6,309,420 B1 | 10/2001 | Preissman | |
| 6,325,992 B1 | 12/2001 | Chow et al. | |
| 6,338,810 B1 | 1/2002 | Carpena et al. | |
| 6,436,143 B1 * | 8/2002 | Ross et al. | 623/17.16 |
| 6,497,901 B1 | 12/2002 | Royer | |
| 6,521,264 B1 | 2/2003 | Lacout et al. | |
| 6,547,866 B1 | 4/2003 | Edwards et al. | |
| 6,562,755 B1 | 5/2003 | Halbrook, Jr. et al. | |
| 6,593,394 B1 | 7/2003 | Li et al. | |
| 6,613,054 B2 | 9/2003 | Scribner et al. | |
| 6,692,563 B2 | 2/2004 | Zimmermann | |
| 6,908,506 B2 | 6/2005 | Zimmermann | |
| 6,953,594 B2 | 10/2005 | Lee et al. | |
| 6,994,726 B2 | 2/2006 | Lin et al. | |
| 7,008,433 B2 | 3/2006 | Voellmicke et al. | |
| 7,115,163 B2 | 10/2006 | Zimmermann | |
| 7,135,027 B2 * | 11/2006 | Delmotte | 606/93 |
| 7,138,442 B2 | 11/2006 | Smith et al. | |
| 7,160,932 B2 | 1/2007 | Schilke et al. | |
| 7,273,523 B2 | 9/2007 | Wenz | |
| 2001/0012968 A1 | 8/2001 | Preissman | |
| 2002/0152929 A1 | 10/2002 | Burgath et al. | |
| 2002/0167480 A1 | 11/2002 | Johnson et al. | |
| 2002/0187104 A1 | 12/2002 | Li et al. | |
| 2002/0191487 A1 | 12/2002 | Sand | |
| 2003/0031698 A1 | 2/2003 | Roeder et al. | |
| 2003/0032964 A1 | 2/2003 | Watkins et al. | |
| 2003/0055512 A1 | 3/2003 | Genin et al. | |
| 2003/0139488 A1 | 7/2003 | Wojciak | |
| 2003/0161858 A1 | 8/2003 | Lidgren | |
| 2003/0180344 A1 | 9/2003 | Wise et al. | |
| 2004/0048947 A1 | 3/2004 | Lidgren et al. | |
| 2004/0122359 A1 | 6/2004 | Wenz et al. | |
| 2004/0157952 A1 | 8/2004 | Soffiati et al. | |
| 2004/0226479 A1 | 11/2004 | Lyles et al. | |
| 2004/0265385 A1 | 12/2004 | West | |
| 2005/0105384 A1 * | 5/2005 | Eder et al. | 366/139 |
| 2005/0142211 A1 | 6/2005 | Wenz | |
| 2005/0199156 A1 | 9/2005 | Khairoun et al. | |
| 2005/0246036 A1 | 11/2005 | Zimmermann | |
| 2005/0256220 A1 | 11/2005 | Lavergne et al. | |
| 2006/0079905 A1 | 4/2006 | Beyar et al. | |
| 2007/0021526 A1 | 1/2007 | He et al. | |
| 2007/0032567 A1 | 2/2007 | Beyar et al. | |
| 2007/0048382 A1 | 3/2007 | Meyer et al. | |
| 2007/0128245 A1 | 6/2007 | Rosenberg et al. | |
| 2007/0191964 A1 | 8/2007 | Preissman | |
| 2007/0254011 A1 | 11/2007 | Schnabelrauch et al. | |

FOREIGN PATENT DOCUMENTS

| | | |
|---|---|---|
| DE | 20218668 | 3/2003 |
| DE | 20218668 U1 | 3/2003 |
| EP | 0473048 A2 | 3/1992 |
| EP | 0511868 A2 | 11/1992 |
| EP | 0520690 A2 | 12/1992 |
| EP | 0543765 A1 | 5/1993 |
| EP | 1002513 A1 | 5/2000 |
| EP | 1255576 B1 | 8/2003 |
| EP | 0835668 B1 | 11/2007 |
| JP | 01320251 | 12/1989 |
| JP | 02116684 | 5/1990 |
| WO | WO9202478 A1 | 2/1992 |
| WO | WO9513835 A1 | 5/1995 |
| WO | WO9614265 A1 | 5/1996 |
| WO | WO0149327 A2 | 7/2001 |
| WO | WO0232827 A1 | 4/2002 |
| WO | WO0236518 A1 | 5/2002 |
| WO | WO03086327 A2 | 10/2003 |
| WO | WO03103734 A1 | 12/2003 |
| WO | WO2004050131 A1 | 6/2004 |
| WO | WO2005009481 A2 | 2/2005 |
| WO | WO2007025633 A2 | 3/2007 |
| WO | WO2007067561 A2 | 6/2007 |

OTHER PUBLICATIONS

Li, Y., et al., "Preparation of amorphous calcium phosphate in the presence of poly(ethylene glycol)," *Journal of Materials Science Letters*, 2003, vol. 22, pp. 1015-1016.

Abdullah et al., Biodegradable Polymeric Bone Cement Formed from Hydroxyapatite, Poly (Propylene Fumerate), Poly (Vinyl Pyrrolidone) and Benzoyl Peroxide, Materials Science and Technology, vol. 20, No. 9, pp. 1084-1086 (2004) (abstract only).

Baroud et al., Influence of Oscillatory Mixing on the Injectability of Three Acrylic and Two Calcium-Phosphate Bone Cements for Vertebroplasty, J Biomed Mater Res, vol. 68B, No. 1, pp. 105-111 (2004) (abstract only).

Beruto et al., Use of Alpha-Tricalcium Phosphate (TCP) as Powders and as an Aqueous Dispersion to Modify Processing, Microstructure, and Mechanical Properties of Polymethylmethacrylate (PMMA) Bone Cements and to Produce Bone-Substitute Compounds, J Biomed Mater Res, vol. 49, No. 4, pp. 498-505 (200) (abstract only).

Bonfield et al., Hydroxyapatite Composite Biomaterials—Evolution and Applications, Materials World, vol. 5, No. 1, pp. 18-20 (1997).

Brown, et al., A new calcium phosphate, water-setting cement, Cements Research Progress 1986 pp. 352-379 (1987).

Canul-Chuil et al., Comparative Study of Bone Cements prepared with either HA or alpha-TCP and Functionalized Methacrylates, J Biomed Mater Res, vol. 64B. No. 1, pp. 27-37 (2003) (abstract only).

Chu et al., Hydroxyapatite/PMMA Composites as Bone Cements, Biomed Mater Eng, vol. 14, No. 1, pp. 87-105 (2004) (abstract only).

Dalby et al., Initial Interaction of Osteoblasts with the Surface of a Hydroxyapatite-Poly (Methylmethacrylate) Cement, Biomaterials, vol. 22, No. 13, pp. 1739-1747 (2001) (abstract only).

Eule et al. Bioactive Bone Cement: The Solution for Osteolysis and Late Implant Loosening, SRS Annual Meeting: Scientific Program Abstracts, pp. 98 (2002).

Frankenburg et al., Evaluation of Hydroxyapatite/Bis-GMA Bone Cement for Fixation of Cemented Hip Stems, The Third Combined Meeting of the Orthopaedic Research Societies of the USA, Canada, Europe and Japan, Hamamatsu City, Japan (1998).

Grigorian et al., Evolution of Tissue Structures in the Mandible after Implantation of Plate from Polymethylmethacrylate and its Compositions with Hydroxyapatite, Stomatolgiia, vol. 82, No. 2, pp. 10-14 (2003) (abstract only).

Harper et al., Tensile Characteristics of Ten Commerical Acrylic Bone Cements, J Biomed Mater Res:Appl Biomater., vol. 53, pp. 605-616 (2000) (abstract only).

Heness et al., Biocomposites—Bone Cement, Hydroxyapatite and Biomimetic Composites for Bone Repair, Innovative Bioceramics, Materials Forum, vol. 27 (2004) (3 page abstract).

Hitchon et al., Comparison of the Biomechanics of Hydroxyapatite and Polymethylmethacrylate Vertebroplasty in a Cadaveric Spinal Compression Fracture Model, J. Neurosurg, vol. 95, Suppl. 2, pp. 215-20, (2001) (abstract only).

Ishikawa et al., Effects of neutral sodium hydrogen phosphate on setting reaction and mechanical strength of hydroxyapatite putty, J Biomed Mater Res, 44, 322-329, 1999.

Ishikawa et al., Non-decay type fast-setting calcium phosphate cement Hydroxyapatite putty containing an increased amount of sodium alginate, J Biomed Mater Res, 36, 393-399, 1997.

Jager et al., Comprehensive Biocompatibility Testing of a New PMMA-hA Bone Cement Versus Conventional PMMA Cement in Vitro, J. Biomater Sci Polym Ed, vol. 14, No. 11, pp. 1283-1298 (2003) (abstract only).

Lee C L et al., Laser Ablation of Dyed Acrylic Bone Cement, Lasers in Surgery and Medicine, Wiley-Liss, New York, US vol. 20, 3, Jan. 1, 1997, pp. 280-289, XP000694435, ISSN:0196-8092.

Lee R.R. et al, Interactions between bone and hydroxyapatite filled 4 META/MMA-TBB adhesive cement in vitro and in physiological environment, 1996, IEEE Xplore, pp. 18-21, entire document.

Li et al., A Novel Injectable Bioactive Bone Cement for Spinal Surgery: A Developmental and Preclinical Study, J Biomed Mater Res, vol. 52, No. 1,,pp. 164-170 (2000) (abstract only).

Liu et al., Influence of the Aspect Ratio of Bioactive Nanofillers on Rheological Behavior of PMMA-Based Orthopedic Materials, J Biomed Mater Res, vol. 71 B, No. 1, pp. 116-22 (2004) (abstract only).

Liao et al., A Fundamental Study on Bioreactions of Sr-HA, Hua Xi Kou Qiang Yi Xue Za Zhi, vol. 20, No. 3, pp. 172-174 183 (2002) (abstract only).

Miyazaki et al., Bioactive PMMA Bone Cement Prepared by Modification with Methacryloxypropyltrimethoxysilane and Calcium Chloride, J Biomed Mater Res, vol. 67A, No. 4, pp. 1417-1423 (2003) (abstract only).

Mousa et al., Biological and Mechanical Properties of PMMA-Based Bioactive Bone Cements, Biomaterials, vol. 21, No. 21, pp. 2137-2146 (2000) (abstract only).

Okada et al., Transmission Electron Microscopic Study of Interface Between Bioactive Bone Cement and Bone: Comparison of Apatite and Wollastonite Containing Glass-Ceramic Filler with Hydroxyapatite and Beta-Tricalcium Phosphate Filler, J Biomed Mater Res, vol. 45, No. 4, pp. 277-284 (1999) (abstract only).

Oonishi et al., Hydroxyapatite Granules Interposed at Bone-Cement Interface in Total Hip Replacements: Histological Study of Retrieved Specimens, J Biomed Mater Res, vol. 53, No. 2, pp. 174-180 (2000) (abstract only).

Patel et al., Comparison of Sintering and Mechanical Properties of Hydroxyapatite and Silicon-Substituted Hydroxyapatite, Key Engineering Materials, 240-242, 919-22 (2003) (abstract only).

Patent Abstract XP-002180738 (1 page total), Park et al., "Compositional effects of CaO—SiO2-P205 bioactive cement on hardening and hydroxyapatite formation" Yoop Hakhoechi, 31(5):502-512 (1994).

Patent Abstract XP-002180739 (1 page total), Nippon Electric Glass Co., "Bone-repair material for fast, strong bonding—contains glass and/or crystalline glass powder, a.q. phosphate solution and bond formation promoter" (1992).

Serbetci et al., Mechanical and Thermal Properties of Hydroxyapatite-Impregnated Bone Cement, Turk J Med Sci, vol. 30, pp. 543-549 (2000) (abstract only).

Turner et al., Hydroxyapatite Composite Resin Cement Augmentation of Pedicle Screw Fixation, Clinical Orthopaedics & Related Research, vol. 1, No. 406, pp. 253-261 (2003) (abstract only).

Wong et al., In Vivo Cancellous Bone Remodeling on a Strontium-Containing Hydroxyapatite (sr-HA) Bioactive Cement, J Biomed Mater Res A, vol. 68, No. 3, pp. 513-521 (2004) (abstract only).).

Wong et al., Ultrastructural Study of Mineralization of a Strontium-Containing Hydroxyapatite (Sr-HA) Cement in Vivo, J Biomed Mater Res A, vol. 70, No. 3, pp. 428-435 (2004) (abstract only.

Zhao et al., Surface Treatment of Injectable Strontium-Containing Bioactive Bone Cement for Vertebroplasty, J. Biomed Mater Res B Appl Biomater, vol. 69, No. 1, pp. 79-86 (2004) (abstract only).

International Search Report, WIPO, Jan. 22, 2009.

International Search Report and Written Opinion, International Application No. PCT/US2007/012723, mailed Dec. 3, 2008.

International Search Report and Written Opinion, International Application No. PCT/US2007/008789, mailed Nov. 13, 2008.

International Search Report and Written Opinion, International Application No. PCT/EP2006/007750, mailed Jun. 11, 2007.

International Search Report, International Application No. PCT/US03/38580, mailed May 19, 2004.

International Search Report, International Application No. PCT/US2005/014616, mailed Sep. 12, 2005.

\* cited by examiner

FIGURE 1

BONE SUBSTITUTE COMPOSITIONS AND METHOD OF USE

CROSS-REFERENCES TO RELATED APPLICATIONS

This application claims the benefit of U.S. Provisional Application No. 60/565,986, filed Apr. 27, 2004, the full disclosure of which is incorporated herein by reference.

FIELD OF THE INVENTION

The present invention relates to bone substitute compositions and methods of use. It further encompasses the use of these novel bone substitute compositions for bone augmentation and the treatment of disease conditions.

BACKGROUND OF THE INVENTION

Vertebral fractures in humans are associated with significant morbidity and mortality. Particularly, there is a relatively high prevalence of osteoporotic vertebral compression fractures (VCFs) in the elderly population, and especially in older women (i.e., aged 50 or older). VCFs are also common in patients on long-term steroid therapy, and in those suffering from multiple myeloma or cancers that have metastasized to the spine. Medical treatment of these fractures may include bed rest, orthotics, and analgesic medications. VCFs can also be caused by trauma, such as an automobile accident or falls. Medical treatment for traumatic fractures may include fusions and fixation with screws, rods and plates.

Vertebroplasty is a procedure in which bone cement is injected into a fractured vertebral body in an attempt to stabilize fractured segments and reduce pain. This procedure was originally used to treat spinal lesions caused by metastases and has recently been used to treat severe bone loss caused by osteoporosis (Eck et al. (Mar. 2002) American J Orthop. 31(3):123-127).

Percutaneous vertebroplasty (PVP) consists of percutaneous injection of a material, such as polymethylmethacrylate, into the fractured vertebral body to produce stability and pain relief. In fact, biomechanical testing has shown that PVP can restore strength and stiffness of the vertebral body to the pre-fracture levels. Moreover, clinical results have indicated some immediate and maintained pain relief in 70-95% of the patients. However, there may be complications which include cement extravasation into the spinal canal or into the venous system.

Kyphoplasty is a new technique, which introduces an expandable body into the vertebral body to reduce the VCF while creating a cavity for the cement injection. This technique has the benefit of sustained vertebral body height restoration and angular deformity correction as well as low pressure delivery of the cement resulting in less extravasation of the cement. Research continues into the development of injectable materials that are resorbable and allow for new bone formation.

Although, vertebroplasty and kyphoplasty are effective in the treatment of osteoporotic VCFs, there is a continuous need for new materials and methods that may allow for a faster return to function and otherwise improve all forms of such medical treatment.

Many bone cements and fillers comprise two components which must be mixed immediately prior to use, often being combined in a syringe just before or during injection. Exemplary syringe systems for injecting such two component materials are shown in copending U.S. application Ser. No. 10/660,465, filed on Sep. 10, 2003, the full disclosure of which is incorporated herein by reference. The need to mix component materials immediately prior to use can complicate the application of such bone filler materials (see U.S. Pat. No. 6,652,887). For example, the mixing of components according to specific protocols can introduce errors prior to injection (e.g., errors in timing, errors in measurement, etc.). Furthermore, the workability or handling characteristics of materials that require mixing is usually fairly short (e.g., less than 30 minutes) once the materials have been combined. Hence, there is a need in the art to provide simpler and improved forms of bone substitute materials which are pre-mixed, pre-filled, ready-for-use, and exhibit an extended workability without the loss of potency. The instant invention addresses this need.

BRIEF SUMMARY OF THE INVENTION

The described compositions and methods include bone substitute compositions and methods of use. Particularly, the compositions include a mineral component and a non-aqueous component. The mineral component hardens in an aqueous environment and the non-aqueous component has an aqueous replacement characteristic that causes the composition to harden when it is replaced with an aqueous fluid. Further provided are methods of bone augmentation and kits.

BRIEF DESCRIPTION OF THE DRAWINGS

The present invention is best understood when read in conjunction with the accompanying figures which serve to illustrate the embodiments. It is understood, however, that the invention is not limited to the specific embodiments disclosed in the figures.

FIG. 1 depicts a kit (4). The kit includes a bone filler device loaded with a pre-mixed bone substitute composition, wherein the bone filler device includes a plunger (1) within a cannula (2). The plunger as depicted is nearly fully engaged within the cannula, thus, providing an accurate depiction of how the device would appear while in use. The bone filler device further includes a cap (3) (e.g., a protective cap). The bone filler device is adapted to deliver the pre-loaded bone substitute composition through the cannula (2) to a bone defect or other location in accordance with the methods of the present invention, as set forth in the instructions for use (5). The kit and the instructions may be stored or shipped in a sterile package (6).

DETAILED DESCRIPTION OF THE INVENTION

The present invention provides bone substitute compositions, including bone fillers, bone components, and the like. It further relates to the use of these novel bone substitute compositions for bone augmentation and the treatment of osteopenia, osteoporosis and other disease conditions such as metastatic disease, and traumatic fractures due to automobile accidents or falls. The compositions and methods described herein offer a multitude of advantages over conventional compositions and methods. One particular advantage is the flowable consistency of the bone substitute composition which allows it to conform perfectly to any bone cavity size. For example, the composition occupies the space in a bone cavity by filling out the space completely in contrast to preformed or granular materials which may result in only partially filled bone cavities (e.g., leaving holes, gaps, etc.). Another advantage is that the bone substitute composition may be pre-mixed with a liquid or other flowable carrier and maintained for extended periods of time prior to use. As such, the material can be pre-loaded into any suitable bone filler device and maintained in a ready-to-use state without loss of potency. Yet, another advantage is the single step procedure for the end user. For example, the end user (e.g., physician, technician, nurse, etc.) may deliver the bone substitute composition to the bone of a patient by employing the pre-loaded bone filler device. The sterilely packaged pre-loaded bone filler device contains the bone substitute composition which is ready for use and can be immediately delivered to the patient without any additional preparation (e.g., no mixing or loading is required) other than optionally heating the composition within the bone filler device. Thus, the material can be delivered to a defective bone or other target site with minimal or no preparation prior to use.

One embodiment provides a composition comprising a mineral component which hardens in an aqueous environment, and a non-aqueous component having an aqueous replacement characteristic that causes the composition to harden when replaced with aqueous body fluid. Optionally, any aqueous fluid may be separately added to the mineral component to effect or enhance hardening of the mineral component in vitro or in vivo. The composition may further comprise a radiopacifier. The radiopacifier can function as a contrast agent.

Another embodiment provides a composition including calcium sulfate and polyethylene glycol (PEG) or other fluids (i.e., non-water containing, but water soluble fluids). Additionally, the invention provides for compositions including calcium phosphates and PEG; and calcium aluminates and PEG. The compositions are stable at room temperature. PEG is replaceable with aqueous body fluid in situ to harden the compositions.

Another embodiment provides a method comprising providing a composition including a mineral component and a non-aqueous component having an aqueous replacement characteristic, and delivering the composition to a bone, wherein the non-aqueous component is replaced with aqueous body fluid, thereby hardening the composition to provide a hardened bone substitute material in contact with the bone. Optionally, an aqueous fluid may be separately added to the mineral component to effect or enhance hardening of the mineral component in vitro or in vivo. The composition may be pre-filled or pre-loaded in a delivery device such as a percutaneous delivery device and may further be delivered through the percutaneous delivery device. A percutaneous delivery device may include, but is not limited to, a bone filler device, a syringe, a needle, a cement gun, a reduced diameter bone filler device, a modified tip to enable directional flow (e.g., side ports) and the like.

Yet, another embodiment provides for a method comprising providing a composition including a mineral component and a non-aqueous component having an aqueous replacement characteristic such as a bone substitute composition, and delivering the composition to a bone, wherein the non-aqueous component such as PEG is replaced with aqueous body fluid, thereby hardening the composition to provide a hardened bone substitute material in contact with the bone. Such a method can be used for bone augmentation. The composition can be delivered to any bone including a defective bone and/or vertebral body. Furthermore, the composition can also be delivered to a bone cavity, a bone void, a bone gap or the like of the skeletal system.

Still, another embodiment provides a method comprising providing a composition including a mineral component and a non-aqueous component having an aqueous replacement characteristic, inserting an expandable device into the bone, and delivering the composition to the bone, wherein the non-aqueous component is replaced with aqueous body fluid, thereby hardening the composition to provide a hardened bone substitute material. This method may optionally include forming a passage into the bone through a guide pin, K-wire, drill, trefine, needle assembly, cannula, stylet, trocar or other suitable instrument. The method may optionally include expanding the expandable device to create a cavity or space within the bone. The expandable device may be a balloon, mechanical jack, or the like. The method may optionally include removing the expandable device from the bone or leaving the expandable device in the bone. For example, the expandable device (e.g., container, implant) can be filled with the composition and the device can be left behind in the bone such as a leave-behind implant like an expandable scaffold or stent. The method can also optionally include inserting a percutaneous delivery device into or near the bone. Such a device includes, but is not limited to, a bone filler device, a syringe, a needle, a cement gun, a reduced diameter bone filler device, a modified tip to enable directional flow (e.g., side ports) and the like.

Another embodiment provides a kit comprising a delivery device such as a percutaneous delivery device, and a composition including a mineral component and a non-aqueous component having an aqueous replacement characteristic such as a bone substitute composition. The percutaneous delivery device contains the composition for delivering the composition to a bone or other location. The pre-loaded percutaneous delivery device provided in the kit may be delivered together with a heat-pack or other heating device. The kit may further contain instructions for use, setting forth a method including providing a composition, and delivering the composition to a bone, wherein a non-aqueous component having an aqueous replacement characteristic is replaced with aqueous body fluid, thereby hardening the composition to provide a hardened bone substitute material in contact with the bone.

The described methods further encompass a method for bone augmentation which comprises providing a kit including a percutaneous delivery device and a composition including a mineral component and a non-aqueous component having an aqueous replacement characteristic (e.g., a bone substitute composition), wherein the composition is ready for use; and delivering the composition to a bone, wherein the non-aqueous component is replaced with aqueous body fluid, thereby hardening the composition to provide a hardened bone substitute material in contact with the bone.

a) Definitions and General Parameters

The following definitions are set forth to illustrate and define the meaning and scope of the various terms used to describe the invention herein.

The terms "composition including a mineral component and a non-aqueous component having an aqueous replacement characteristic" or "bone substitute composition" are used interchangeably herein and refer to a material that is capable of replacing natural bone to various degrees in any bone including a defective bone or vertebral body as well as a bone cavity, bone void, bone gap or the like of the skeletal system. Representative bones include, but are not limited to, vertebral bodies, long bones such as the femur, tibia, humerus, radius, and other bones such as the calcaneous and pelvis. For example, a bone substitute composition may serve as a bone graft, bone filler, bone component, or any other bone replacement material, whether or not intrinsic to the structural stability and/or weight bearing ability of the bone. A bone substitute composition may be employed during bone augmentation or as a treatment for any osteopenic or orthopedic disease condition (e.g., osteoporotic vertebral compression fractures (VCFs) and others).

The term "delivering a bone substitute composition to a bone" encompasses the delivery of a bone substitute composition to a bone, into a bone, near a bone, within a bone, adjacent to a bone, into the proximity of a bone, and the like. As such, the bone substitute composition may serve as a bone graft (e.g., to provide a bone replacement), bone filler (e.g., to fill a bone cavity, void or gap; or a crack on the surface of a bone), bone component, or any other bone replacement material (e.g., to fuse one or more bones), whether or not intrinsic to the structural stability and/or weight bearing ability of the bone.

The term "mineral component" means, for the purpose of the specification and claims, a substance, typically an inorganic substance, that may be used as a primary component of a bone substitute composition. The mineral component of the instant invention remains flowable in certain non-aqueous environments but hardens in an aqueous environment. The mineral component may be one or more mineral salts, including but not limited to, calcium sulfate, calcium sulfate α-hemihydrate, calcium sulfate β-hemihydrate, calcium sulfate anhydrous and mixtures thereof. Other suitable mineral salt compositions are mixtures of magnesium hydroxyphosphate, tri-magnesium phosphate, di-ammonium hydroxyphosphate, di-ammoniumsulfate, di-potassium hydroxyphosphate, potassium di-hydroxyphosphate, and di-sodium-, sodium-di-hydroxyphosphate. Still other suitable compositions are magnesium oxide in combination with salts of divalent metals such as magnesium carbonate ($MgCO_3$); and combinations of silicon dioxide ($SiO_2$), aluminum oxide ($Al_2O_3$), iron oxide ($Fe_2O_3$) and calcium oxide (CaO). Suitable combinations may be further combined with sodium aluminate for reaction enhancement. Additional suitable mineral components are calcium phosphates (e.g., tri-calcium phosphate, tetra-calcium-phosphate and di-calcium-phosphate) and calcium aluminates. The preferred mineral component is calcium sulfate, including calcium sulfate-anhydrous, calcium sulfate α-hemihydrate, calcium sulfate β-hemihydrate, and calcium sulfate-dihydrate. A preferred combination includes calcium sulfate anhydrous with calcium sulfate-dihydrate. Another preferred combination includes calcium sulfate α-hemihydrate with calcium sulfate-dihydrate. Yet another preferred combination includes calcium sulfate-anhydrous with calcium sulfate α-hemihydrate and calcium sulfate-dihydrate. Still another preferred combination includes calcium sulfate β-hemihydrate with calcium sulfate-dihydrate.

A "a non-aqueous component having an aqueous replacement characteristic" refers to a liquid, gel, slurry, or other material, that has a relatively high viscosity and serves as a carrier for a mineral component (supra) of the instant invention. In particular, the non-aqueous component is a viscosity enhancing agent that is able to solubilize or suspend the mineral component in a liquid or other flowable form to permit delivery into a desired target site in a bone, between bones, or to a void or gap in the skeletal system to cause the healing of the bone or fusion of adjacent bony structures. The non-aqueous component is further selected to inhibit or prevent hardening of the mineral component when the mineral component is present in the non-aqueous component. Specifically, the hardening of the mineral component occurs because the non-aqueous component is diluted out during the entrance of water in the aqueous body fluid, wherein the water reacts with the inorganic mineral component leading to a hardened composition. Exemplary non-aqueous components include, but are not limited to, polyethylene glycol (PEG); polyalcohol like glycerin or polyvinyl alcohol; polyvinylpyrolidon (PVP); propandiol; propanol; materials from the group of glycosaminoglycans (GAGs); chondroitin sulfate; dextran; dextran sulfate; chitosan; polylactic acid (PLA); polyglycolic acid (PGA); and polylacticglycolic acid (PLGA). PEG may range from molecular weight (MW) 100 to 10,000. Notably, PEG with a MW greater than 600 may require heat pre-treatment in order to result in a soft flowing material.

The term "aqueous body fluid", as used herein, means any liquid substance containing water that exists inside or outside the body of an organism. The aqueous body fluid may be extracted, excreted, or secreted from an organism or a tissue of an organism. Preferably, the aqueous body fluid is found in situ. Aqueous body fluids of relevance to the present invention include, but are not limited to, water, blood, serum, plasma, urine, cerebral spinal fluid, tears, and amnionic fluid. The aqueous body fluid may or may not contain cells.

The term "stable", as used herein, refers to a composition that remains unchanged in terms of its consistency, applicability and effectiveness during manufacture (sterilization) and storage. Such a "stable composition" may be sterilized using a variety of methods (such as gamma irradiation, ethylene oxide), and subsequently stored at room temperature or under controlled conditions (such as refrigeration, heat, vacuum and the like) in any suitable sealed container without exhibiting signs of degradation. The temperate range under which the composition remains stable ranges from about −10° C. to about 60° C. For example, the composition is stable at a temperature range from about 0° C. to about 50° C. Preferably, the composition is stored at an ambient temperature range from about 4° C. to about 37° C.

The phrase "ready for use" in the context of this invention means, a bone substitute composition that may be readily delivered to a bone or vertebral body or other suitable site within the body of a patient (e.g., for treatment, improvement, support, etc.) without the need of additional components and/or mixing steps other than any physical device(s) that may aid in the delivery of the composition.

b) Bone Substitute Compositions

One embodiment provides a bone substitute composition comprising a mineral component which hardens in an aqueous environment, and a non-aqueous, flowable component, wherein the non-aqueous component has an aqueous replacement characteristic that causes the composition to harden when replaced with aqueous body fluid. Optionally, an aqueous fluid may be separately added to the mineral component to effect or enhance hardening of the mineral component in vitro or in vivo. The bone substitute composition may further comprise a radiopacifier which can act as a contrast agent. Examples are radiopacifiers as disclosed in DE 202 18668.7 and incorporated herein by reference. The mineral component includes, but is not limited to, calcium sulfate, calcium sulfate α-hemihydrate, calcium sulfate β-hemihydrate, calcium sulfate anhydrous, calcium sulfate-dihydrate, magnesium hydroxyphosphate, tri-magnesium phosphate, di-ammonium hydroxyphosphate, di-ammonium sulfate, di-potassium hydroxyphosphate, potassium di-hydroxyphosphate, di-sodium-, sodium-di-hydroxyphosphate, magnesium carbonate, silicon dioxide, aluminum oxide, iron oxide, calcium oxide, calcium phosphates such as tri-calcium phosphate, tetra-calcium phosphate and di-calcium phosphate, and calcium aluminate. In a preferred embodiment, the mineral component is calcium sulfate which further includes calcium sulfate-anhydrous and calcium sulfate-dihydrate. For example, calcium sulfate—anhydrous maybe be combined with at least one seed of calcium sulfate-dihydrate, and more preferably seeds of calcium sulfate-dihydrate. In another preferred embodiment, the mineral component is calcium sulfate which further includes calcium sulfate α-hemihydrate or calcium sulfate β-hemihdyrate in combination with calcium sulfate-dihydrate. Similarly, calcium sulfate α-hemihydrate or calcium sulfate β-hemihdyrate may be combined with at least one seed of calcium sulfate-dihydrate, and more preferably seeds of calcium sulfate—dihydrate. In another preferred embodiment, the mineral component includes calcium sulfate-anhydrous, calcium sulfate α-hemihydrate and calcium sulfate-dihydrate. In another embodiment, the mineral component includes calcium phosphates or calcium aluminates. The non-aqueous component includes, but is not limited to, polyethylene glycol (PEG), glycerin, polyvinylalcohol, polyvinylpyrolidon (PVP), propandiol, propanol, glycosaminoglycan (GAG), C-chondroitinsulfate, dextran, dextran sulfate, chitosan, polylactic acid (PLA), polyglycolic acid (PGA), polylacticglycolic acid (PLGA), poly-L-lactide (PLLA), and combinations thereof. In a preferred embodiment, the non-aqueous component is PEG (e.g., MW 100-10,000). Preferably, PEG has a molecular weight (MW) of about 100 to about 2,500. More preferably, PEG has a MW of about 150 to about 2,000. Most preferably, PEG has a MW of about 200 to about 1,500. In one embodiment, flowable PEG has a higher viscosity and a MW from about 100 to about 500. For example, the preferred MW is about 200 for flowable cements. In another embodiment, non-flowable PEG has a lower viscosity and a MW from about 600 to about 10,000. For example, the preferred MW is about 1500 for non-flowable, waxy cements.

The bone substitute composition (e.g., bone cement) may be pre-loaded in a suitable device prior to use and is, thus, subject to easy handling and fast and convenient preparation. Material related or procedural failures are practically non-existent because of the ready-to-use nature of the composition. Furthermore, the viscous consistency of the composition ensures that all the bone substitute material is released to the bone (e.g., bone cavity, vertebral body, etc.) during the delivery process.

The bone substitute composition is stable at room temperature and other controlled conditions (e.g., refrigeration, vacuum, etc.). The ratio of PEG to the inorganic hardening compounds may vary according to the compounds used. In one embodiment, the composition preferably includes, but is not limited to, about 10 weight percent to about 50 weight percent PEG; about 30 weight percent to about 80 weight percent calcium sulfate-anhydrous, and about 0 weight percent to about 60 weight percent calcium sulfate-dihydrate. Herein, the sum of all weight percentages is 100. In another embodiment, the composition preferably includes, but is not limited to, about 20 weight percent to about 40 weight percent PEG; about 80 weight percent to about 60 weight percent calcium sulfate α- or β—hemihydrate, and about 0 weight percent to about 40 weight percent calcium sulfate-dihydrate. In another embodiment, the composition preferably includes mixtures of calcium sulfate-anhydrous with calcium sulfate α-hemihydrate in any mixture including about 0 weight percent to about 25 weight percent calciumsulfate-dihydrate. In a preferred embodiment the composition includes PEG, calcium sulfate-anhydrous, calcium sulfate α-hemihydrate, and calcium sulfate-dihydrate. Particularly, the composition may include PEG, calcium sulfate-anhydrous, calcium sulfate α-hemihydrate, and about 0 weight percent to about 25 weight percent calcium sulfate-dihydrate. In a preferred embodiment, the composition may be pre-mixed and further pre-loaded in a suitable device prior to use. Furthermore, the instant composition may include PEG which is replaceable with aqueous body fluid to harden the composition. PEG is a biocompatible polymer which allows calcium sulfate particles to flow smoothly. PEG is also highly water soluble. Due to this high water solubility, the addition of water allows for a fast reaction with the inorganic polymer. When PEG comes in contact with water or any body fluid, it is diluted out and the entrance of the water or body fluid causes the hardening of the calcium sulfate. Typical hardening or crystallization times of the bone substitute composition range from about 15 minutes to about 360 minutes, and more usually range from about 15 minutes to about 240 minutes, and most usually range from about 15 minutes to about 120 minutes.

c) Methods of Use

One embodiment provides a method comprising providing a composition including a mineral component (e.g., calcium sulfate, calcium phosphate, calcium aluminate, etc.) and a non-aqueous component with an aqueous replacement characteristic (e.g., PEG), and delivering the composition to a bone, wherein the non-aqueous component is replaced with aqueous body fluid, thereby hardening the composition to provide a hardened bone substitute material (e.g., in the bone cavity, vertebral body, defective bone, etc.). This method is suitable for bone augmentation. Optionally, an aqueous fluid may be separately added to the mineral component to effect or enhance hardening of the mineral component in vitro or in vivo. The composition may be pre-filled in a delivery device (e.g., percutaneous delivery device) and may further be delivered through the delivery device. Thus, a percutaneous delivery device may be pre-loaded with the composition. A percutaneous delivery device may include, but is not limited to, a bone filler device, a syringe, a needle, a cement gun, a reduced diameter bone filler device, a modified tip to enable directional flow (e.g., side ports) and the like. Such delivery devices are described in U.S. Pat. Nos. 6,241,734; 6,048,346; 6,641,587; 6,719,761; and 6,645,213 which are incorporated herein by reference in their entirety.

Figure 1:
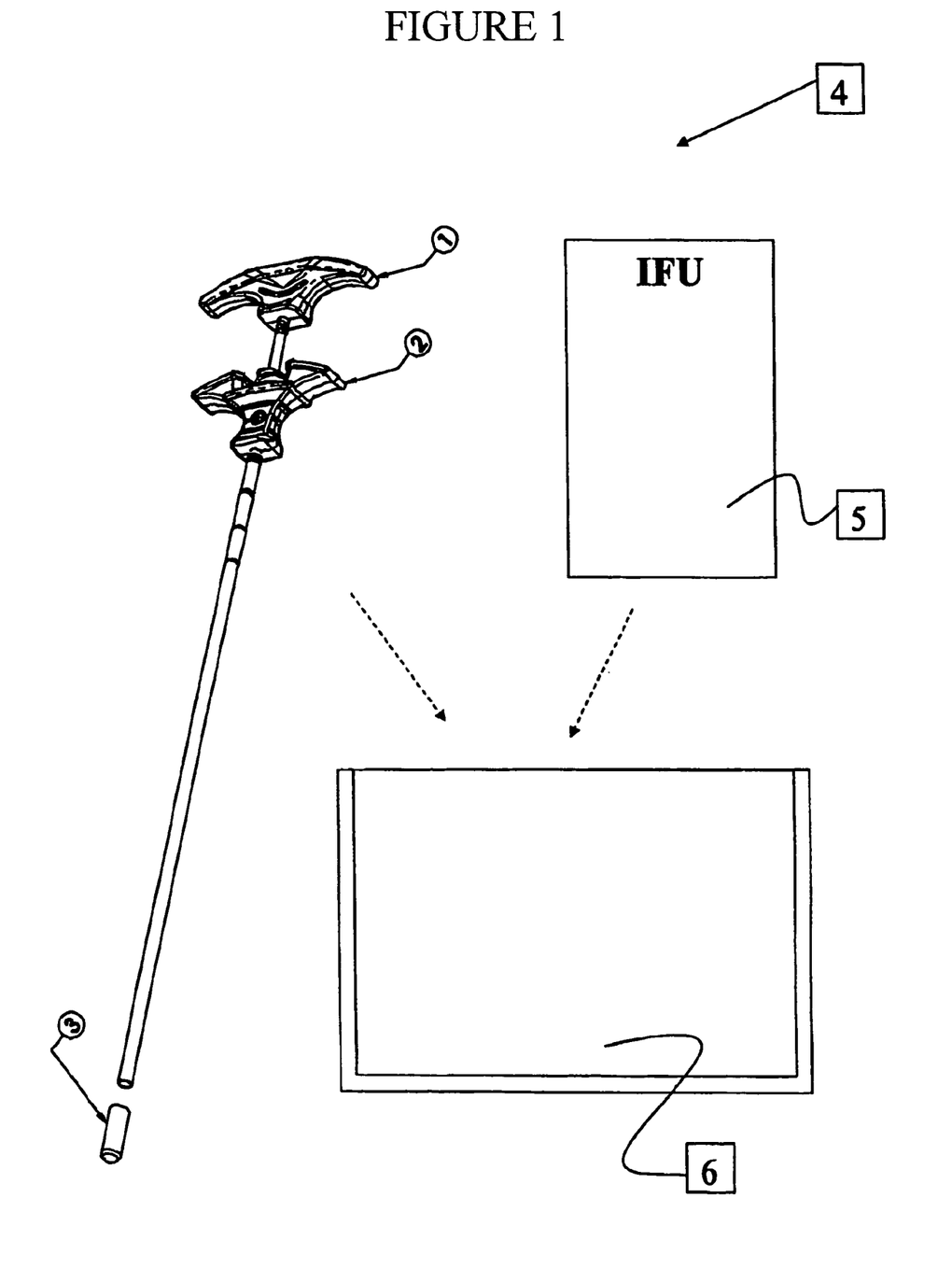

In another embodiment, the bone substitute composition is injected into or near a bone through a syringe. Preferably, a sterile syringe is pre-loaded with the composition. The syringe can be pre-loaded with calcium sulfate mixed with PEG (e.g., pre-mixed composition) in order to achieve the appropriate consistency and flowability. Surprisingly, the material in the syringe stays in a highly viscous and cohesive state even at body temperature. Due to the strong cohesiveness of the material, there is practically no risk of extravasation when the material is transferred into the body, making this composition highly desirable for use as a bone substitute. In a preferred embodiment, the bone substitute composition is delivered to the bone through a bone filler device as shown in FIG. 1. The bone filler device includes a cannula (2) (e.g., tube or nozzle) which contains the pre-loaded bone substitute composition, and a separate plunger (1) which is used to expel the material from the cannula. The kit, which may include a plurality of bone filler devices with instructions for use (IFU) within a sterile package, can be conveniently shipped or mailed. During shipment of the kit, the cap (3) would be found at the distal end of the cannula (2) in order to protect the pre-mixed bone substitute composition within the cannula. A second cap (not shown) such as a standard locking luer cap or the like would screw onto the proximal end of the cannula (2) further maintaining the integrity of the pre-mixed bone substitute composition within the cannula (2). The bone filler device is adapted to deliver the pre-mixed bone substitute composition (high viscosity, medium viscosity, etc.) through the cannula, tube, or nozzle to a bone defect or other location in accordance with the methods of the present invention, as set forth in the instructions for use (5). The kit and the instructions may be stored in the sterile package (6) prior to use for any desired period of time.

At a low viscosity the paste is pushed out of a syringe or bone filler device, for example, by means of a plunger, tamp or rod (i.e., an instrument used to occlude a hollow cannula), wherein the specific force is about 100 N maximum. As such, not more than 70 weight percent of inorganic reactant is admixed to the polyalcohol (e.g., PEG). At a high viscosity the paste does not flow through a syringe and the force to push the paste out of the syringe or bone filler device is much higher than 100 N. Thus, at a high viscosity more than 70 weight percent of the inorganic reactant is admixed to the organic solvent which is free of water (e.g, PEG). Additionally, high viscosities can be achieved by using PEGs of higher molecular weight (MW) (i.e., higher than MW 600). In order to apply a paste that contains, for example PEG with a MW greater than 600, a heat pack or other means of heat (e.g., microwave irradiation, warm water bath, etc.) is required to bring the material into a flowable state, where it can then be delivered by a bone filler device (as shown in FIG. 1), a reduced diameter bone filler device, a syringe, a needle, a cement gun, a variable rate cement gun, a modified tip to enable directional flow (e.g., side ports) and the like. Particularly, after heat is briefly applied to the mixture, PEG melts like wax and flows. The cannula can be inserted into or near the bone and the composition can be delivered accordingly. Similarly, the bone filler device can be pre-filled with calcium sulfate mixed with PEG (e.g., pre-mixed composition) in order to achieve the appropriate consistency and flowability. As in any suitable device, the material in the bone filler device stays in a highly viscous state even at body temperature and can easily be delivered to the bone without extravasation or loss of bone substitute material.

Another embodiment provides a method comprising providing a composition including a mineral component and a non-aqueous component, inserting an expandable device into the bone, and delivering the composition to the bone through a delivery device (e.g., percutaneous delivery device), wherein the non-aqueous component is replaced with aqueous body fluid, thereby hardening the composition to provide a hardened bone substitute material. Such a method can be employed for bone augmentation.

Another embodiment provides a method which includes a series of steps. An incision is formed in a body of a patient and a bone or vertebral body is penetrated with an instrument such as a needle assembly, cannula, stylet, guide pin, K-wire, drill, trefine, trocar, or other suitable instrument. Then, the bone marrow of the bone is optionally drilled to enlarge the bone cavity, space or passage to be treated. This is followed with an expandable device, such as a balloon, which is inserted in the bone cavity and expanded. The expansion of the balloon causes a compacting of the cancellous bone against the inner surface of the cortical bone to be treated to further enlarge the cavity. Then, a flowable bone substitute composition is introduced into the bone cavity (e.g., via a syringe, bone filler device, or other device) and allowed to set to a hardened condition. Following this, the instruments are removed and the incision in the skin is covered with a bandage. A detailed description of this method is provided in U.S. Pat. Nos. 5,108,404 and 4,969,888, which are incorporated herein by reference in their entirety. Alternatively, the method can be practiced with a leave-behind implant such as an expandable scaffold or stent.

Alternative methods for making cavities in bones include, but are not limited to, cutting/scraping with a curette or osteotome, rotating blades, chisels; using radio frequency, electrical energy, ultrasonic waves, water jets, thermal energy, cryoablation, laser; and chemical solutions. Such methods can be used in conjunction with the bone substitute compositions of the instant invention.

Yet another embodiment provides a method for bone augmentation comprising providing a kit (described below) including a percutaneous delivery device and a bone substitute composition, wherein the composition is ready for use; and delivering the composition to a bone (defective bone, bone cavity, vertebral body, etc.) wherein the non-aqueous component (e.g., PEG) is replaced with aqueous body fluid, thereby hardening the composition to provide a hardened bone substitute material in contact with the bone. The preloaded delivery device provided in the kit may be provided together with a heat-pack or other heating device. After activation of the heat-pack, the delivery device which includes the material (i.e., the bone substitute composition) is heated up allowing for the composition to become flowable for easy introduction to the bone.

Generally, PEGs with a molecular weight (MW) greater than 600 are no longer at a liquid state but have a wax-like consistency at room temperature. In higher viscosity bone substitute compositions, PEG preferably has a MW of about 600 to about 10,000. More preferably, PEG has a MW of about 800 to about 2,000. Most preferably, PEG has a MW of about 1,000 to about 1,500. Preheating the PEG will liquefy the composition to a paste-like material and, thus, make it more flowable. During production (i.e., prior to use by the end user), a delivery device can be pre-loaded by admixing the hardening mineral component to a preheated PEG with a MW greater than 600 to create the bone substitute composition. Once PEG cools down, the composition becomes more viscous in the delivery device and will achieve a wax-like consistency. At this point, the composition is stable and ready for storage or delivery to the end user. The end user may then immediately use the composition to treat a patient, wherein some compositions require a higher temperature to liquefy the PEG. The temperature to liquefy the PEG may range from about 50° C. to about 90° C. Particularly, the application of a heat-pack (or other form of heat) around the delivery device will heat up the PEG and change its wax-like consistency into a more flowable, liquefied state again, after which the material can then be extruded out of the delivery device. Notably, the composition changes to a lower viscosity state due to the heating mechanism, thereby allowing easy extrusion of the respective material from the delivery device to the bone or vertebral body. Once delivered, the material changes back to a highly viscous state at body temperature and then hardens in vivo. Specifically, the hardening of the inorganic material occurs because the polymer (e.g. PEG) is diluted out during the entrance of water in the aqueous body fluid, wherein the water reacts with the inorganic mineral component leading to a hardened composition. In particular, the entrance of the water and dilution of the polymer happen simultaneously. In this example of a higher molecular weight PEG as the non-aqueous component, in combination with a mineral component, the flow and hardening properties depend on the temperature-dependent viscosity of PEG, the water solubility of PEG, and the aqueous hardening of the mineral component. Upon heating above body temperature, the composition is flowable and can be delivered to a bone cavity, where the composition will conform to the geometry of the cavity. Upon cooling to body temperature, PEG stiffens to a wax-like consistency, thereby maintaining the natural conformation to the cavity. Subsequently, PEG comes in contact with aqueous body fluid and is diluted out thus causing the hardening of the mineral component to it ultimate hardened crystalline state. Preferred are highly viscous polymers with high water solubility in combination with inorganic reactive fillers or substitutes. The inorganic fillers or substitutes (e.g., calcium sulfate, etc.) react with water or other body fluids after dissolution of the polymer. As such, fast reacting compounds achieve good results. One notable advantage of the composition is that it cools down in the body relatively quickly, thereby returning to its stiff and wax-like consistency within a short period of time. This provides the bone with immediate support and adds to the bone's mechanical strength.

d) Kits Employing Bone Substitute Compositions

In one embodiment, a kit is provided. The kit comprises a delivery device such as a percutaneous delivery device, and a bone substitute composition, including a mineral component and a non-aqueous component. In a preferred embodiment, the composition includes calcium sulfate-anhydrous, calcium sulfate-dihydrate, and a non-aqueous component. In another preferred embodiment, the composition includes calcium sulfate α- or β-hemihydrate, calcium sulfate-dihydrate, and a non-aqueous component. In another preferred embodiment, the composition includes calcium sulfate-anhydrous, calcium sulfate α-hemihydrate, calcium sulfate-dihydrate, and a non-aqueous component. In another embodiment, the compositions include calcium phosphate and PEG; and calcium aluminate and PEG. The non-aqueous component may include, but is not limited to, polyethylene glycol (PEG), glycerin, polyvinylalcohol, polyvinylpyrolidon (PVP), propandiol, propanol, glycosaminoglycan (GAG), C—chondroitinsulfate, dextran, dextran sulfate, chitosan, polylactic acid (PLA), polyglycolic acid (PGA), polylacticglycolic acid (PLGA), poly-L-lactide (PLLA), and combinations thereof. The kit may further include instructions for use. Particularly, the instructions may set forth a method comprising providing the composition; and delivering the composition to a bone, wherein the non-aqueous component is replaced with aqueous body fluid, thereby hardening the composition to provide a hardened bone substitute material in contact with the bone. The percutaneous delivery device provided in the kit may be pre-loaded with the bone substitute composition and delivered together with a heat-pack or other heating device (supra). In a preferred embodiment, the delivery device may be sterilely packaged. The delivery device may be a bone filler device, a syringe, a needle, a cement gun, a reduced diameter bone filler device, a modified tip to enable directional flow (e.g., side ports) and the like. In another preferred embodiment, the kit provided includes a bone substitute composition that is ready for use.

In another embodiment, the kit includes a syringe loaded with the composition for injecting the composition into a bone cavity or vertebral body. An exemplary kit including a syringe pre-loaded with a pre-mixed bone substitute composition, instructions for use (IFU), and a sterile package. The syringe is adapted to deliver a pre-mixed bone substitute composition through a needle or cannula to a bone or other location in accordance with the methods of the present invention, as set forth in the instructions for use. The package may be any conventional medical device package, such as a box, pouch, tube, or the like. The syringe is preferably sterilely maintained within the package so that it can be used without further sterilization. Optionally, a heat pack may be included in the kit.

In a preferred embodiment, the kit includes a bone filler device loaded with the composition for delivering the composition to a bone cavity or vertebral body. This exemplary kit (4), including a bone filler device pre-loaded with a bone substitute composition is illustrated in FIG. 1. The bone filler device may be a two-piece instrument (i.e., an assembly). As such, the bone filler device includes a cannula (2) (e.g., tube or nozzle) which contains the pre-loaded bone substitute composition, and a separate plunger (1) which is used to expel the material from the cannula. One type of bone filler device can be used for various different viscosity ranges of the material to be expelled. Optionally, different sizes of delivery cannulas may be used depending on the viscosity ranges (e.g., a specific bone filler device for a composition with a high viscosity and specific bone filler device for a composition with a medium viscosity). The kit, which includes the bone filler device with instructions for use (IFU) within a sterile package, can be conveniently shipped or mailed. During shipment of the kit, the cap (3) would be found at the distal end of the cannula (2) in order to protect the pre-loaded bone substitute composition within the cannula. Furthermore, the device would also include a standard locking luer cap that screws onto the proximal end of the cannula (not shown). Thus, during shipment, the cannula would be pre-loaded with the bone substitute composition with caps at both ends and packaged with a separate plunger (1) within a sterile package (6) and instructions for use (IFU) (5) according to the present invention. Furthermore, multiple pre-loaded or pre-filled cannulas (2) (not shown) can be provided in the kit. Each cannula (2) holds a specific amount of the pre-loaded bone substitute composition (e.g, approximately 1.5 cc) and approximately six pre-loaded bone filler devices may be shipped in one kit in order to fill one cavity in a vertebral body. Cavity volumes may vary depending on the size of the vertebral body and on how much expansion of the expandable body is achieved. The molded handles on the distal ends of the cannula (2) and plunger (1) assist in the finger gripping and expelling of material through the device (see FIG. 1). The bone filler device is adapted to deliver the pre-mixed bone substitute composition (high viscosity, medium viscosity, etc.) through the cannula, tube, or nozzle to a bone or other location in accordance with the methods of the present invention, as set forth in the instructions for use (5). The kit and the instructions for use may be stored in the sterile package (6) prior to use for any desired period of time. The package (6) may be any conventional medical device package, such as a box, pouch, tube, or the like. The bone filler device is preferably sterilely maintained within the package so that it can be used without further sterilization. Optionally, a heat pack may be included in the kit.

e) Examples

The following specific examples are intended to illustrate the invention and should not be construed as limiting the scope of the claims.

Example 1

14 g of $CaSO_4$-hemihydrate and 0.5 g $CaSO_4$-dihydrate were admixed to 4.4 g PEG 400 with a spatula. The paste was transferred into a syringe. Then the paste was transferred into several 6 mm diameter×12 mm length cylindrical cavities formed in a highly porous polyurethane sponge to create a mold. The mold was immersed in a saline solution at 37° C. for 24 hours. The cylindrical test specimens were then compressed in a ZWICK material testing machine with a cross-head speed of 1 mm/min. The compressive strength of the resulting specimens was determined to be about 9.27 MPa.

Example 2

A paste was produced by adding 12.89 g of a powder mixture of 62.5% TCP, 12.5% di-sodium hydroxyl-phosphate ($Na_2HPO_4$), 12.5% di-ammonium-hydroxy-phosphate and 12.5% $Mg_3(PO_4)_2$ to 5.81 g glycerol. The paste hardened during incubation in a warm saline solution that was kept at 37° C.

Example 3

A paste was produced by admixing 8.7 g of the powder mixture of Example 2 to 7 g of heated PEG 1500. The paste hardened during incubation in a warm saline solution that was kept at 37° C.

Example 4

A paste was produced by admixing a powder made from 57 weight percent (wt %) $Mg_3(PO_4)_2$ and 43 wt % $(NH_4)_2HPO_4$ with 5.40 g PEG 400. Prior to admixing the powder into the PEG, the powder was mixed and milled in a planetary ball mill. The paste was transferred into a syringe. Then the paste was transferred into several 6 mm diameter×12 mm length cylindrical cavities formed in a highly porous polyurethane sponge to create a mold. The mold was immersed in a saline solution at 37° C. for 18 hours. The cylindrical test specimens were then compressed in a ZWICK material testing machine with a cross-head speed of 1 mm/min. The compressive strength of the resulting specimens was determined to be 5.86±0.34 MPa.

Example 5

A powder mixture of the following composition: 35 g $Al_2O_3$+14 g CaO+11 g $SiO_2$+20 g hydroxyapatite+4 g $CaCl_2$ was mixed and milled in a planetary ball mill at 400 RPM for 15 minutes. In order to obtain a paste, 14.20 g of the ground powder was admixed to 6.70 g PEG 400. This paste was transferred into a syringe. Then the paste was transferred into several 6 mm diameter×12 mm length cylindrical cavities formed in a highly porous polyurethane sponge to create a mold. The mold was immersed in a saline solution at 37° C. for 72 hours. The cylindrical test specimens were compressed in a ZWICK material testing machine with a cross-head speed of 1 mm/min. The compressive strength of the resulting specimens was determined to be 11.77±1.08 MPa.

Example 6

17 g of the powder mixture of Example 5, wherein the 20 g hydroxyapatite in the formulation were replaced with calcium sulfate α-hemihydrate, were admixed to 5.60 g PEG 400. This paste was transferred into a syringe. Then the paste was transferred into several 6 mm diameter×12 mm length cylindrical cavities formed in a highly porous polyurethane sponge to create a mold. The mold was immersed in a saline solution at 37° C. for 72 hours. The cylindrical test specimens were then compressed in a ZWICK material testing machine with a cross-head speed of 1 mm/min. The compressive strength of the resulting specimens was determined to be 23.04±2.51 MPa.

Example 7

A powder mixture was prepared, including the following: 35 g $Al_2O_3$, 14 g CaO, 1 g $SiO_2$, 20 g $CaTiO_3$ and 0.07 g LiCl. The powder mixture was milled in a planetary ball mill at 250 RPM for 15 minutes. 8.86 g from the resulting powder was mixed into 3 g glycerol. The resulting paste was transferred into a syringe. Then the paste was transferred into several 6 mm diameter×12 mm length cylindrical cavities formed in a highly porous polyurethane sponge to create a mold. The mold was immersed in a saline solution at 37° C. for 72 hours. The cylindrical test specimens were compressed in a ZWICK material testing machine with a cross-head speed of 1 mm/min. The compressive strength of the resulting specimens was determined to be 33.41±10.22 MPa.

In order to enhance the radiopacity, especially of the powder compositions in examples 4, 5 and 6, any of the following can be admixed in weight ratios of 0-20%:

Benitoit=$BaTi[Si_3O_9]$
Barysilit=$Pb_3[Si_3O_9]$
Thortveitit=$Sc_2[Si_3O_9]$
Phenakit=$Be_2[SiO_4]$
Willemit=$Zn_2[SiO_4]$
Olivin=$(Mg,Fe)_2[SiO_4]$
Zirkon=$Zr[SiO_4]$
Hemimorphit=$Zn_4[Si_2O_7].H_2O$
Radiopacifiers Various modifications and variations of the present invention will be apparent to those skilled in the art without departing from the scope and spirit of the invention. Although the invention has been described in connection with specific preferred embodiments, it should be understood that the invention as claimed should not be unduly limited to to such specific embodiments. Indeed, various modifications of the described modes for carrying out the invention which are obvious to those skilled in the art are intended to be within the scope of the claims.

What is claimed is:

1. A bone cement composition consisting essentially of:
   a mineral component that hardens in an aqueous environment, wherein said mineral component is selected from the group consisting of calcium sulfate-anhydrous, calcium sulfate-dihydrate, calcium sulfate α-hemihydrate, calcium sulfate β-hemihydrate, and combinations thereof; and
   a non-aqueous component having an aqueous replacement characteristic that causes the composition to harden to a crystalline state in vivo when the non-aqueous component is replaced with aqueous body fluid.

2. The composition of claim 1, wherein said composition further comprises a radiopacifier.

3. The composition of claim 1, wherein said non-aqueous component is selected from the group consisting of polyethylene glycol (PEG), glycerin, polyvinylalcohol, polyvinylpyrolidon (PVP), propandiol, propanol, glycosaminoglycan (GAG), C-chondroitinsulfate, dextran, dextran sulfate, chitosan, polylactic acid (PLA), polyglycolic acid (PGA), polylacticglycolic acid (PLGA), poly-L-lactide (PLLA), and combinations thereof.

4. The composition of claim 3, wherein said PEG has a molecular weight (MW) of about 200 for flowable cements and about 1500 for non-flowable cements.

5. A bone cement composition consisting essentially of:
   calcium sulfate-anhydrous;
   calcium sulfate-dihydrate; and
   polyethylene glycol (PEG), wherein said PEG is replaced with aqueous body fluid in situ to harden said composition to a crystalline state in vivo.

6. The composition of claim 5, wherein said composition is stable at a temperature range from about 0° C. to about 50° C.

7. The composition of claim 5, wherein said calcium sulfate-anhydrous is a powder and said calcium sulfate-dihydrate consists of at least one seed.

8. The composition of claim 5, wherein the composition comprises about 10 weight percent to about 50 weight percent PEG; about 30 weight percent to about 80 weight percent calcium sulfate-anhydrous, and about 0 weight percent to about 60 weight percent calcium sulfate-dihydrate.

9. The composition of claim 5, wherein the calcium sulfate-anhydrous comprises calcium sulfate α- or β-hemihydrate.

10. The composition of claim 9, wherein the composition comprises about 20 weight percent to about 40 weight percent PEG; about 80 weight percent to about 60 weight percent calcium sulfate α- or β-hemihydrate, and about 0 weight percent to about 40 weight percent calcium sulfate-dihydrate.

11. A bone cement composition consisting essentially of:
    calcium sulfate-anhydrous;
    calcium sulfate α-hemihydrate;
    calcium sulfate-dihydrate; and p
    polyethylene glycol (PEG), wherein said PEG is replaced with aqueous body fluid to harden said composition to a crystalline state in vivo.

12. The composition of claim 11, wherein said calcium sulfate-dihydrate is about 0 to about 25 weight percent.

13. A method comprising:
    providing a composition consisting essentially of:
    a mineral component that hardens in an aqueous environment, wherein said mineral component is selected from the group consisting of calcium sulfate-anhydrous, calcium sulfate-dihydrate, calcium sulfate α-hemihydrate, calcium sulfate β-hemihydrate, and combinations thereof; and
    a non-aqueous component having an aqueous replacement characteristic that causes the composition to harden to a crystalline state when the non-aqueous component is replaced with aqueous body fluid; and
    delivering said composition to a bone, wherein said non-aqueous component is replaced with aqueous body fluid, thereby hardening said composition to a crystalline state in vivo to provide a hardened bone substitute material in contact with the bone.

14. The composition of claim 13, wherein said composition is pre-mixed prior to use.

15. The composition of claim 14, wherein said composition is further pre-loaded in a percutaneous delivery device prior to use and delivered through the device.

16. A method comprising:
    providing a bone cement composition consisting essentially of a mineral component, wherein said mineral component is selected from the group consisting of calcium sulfate-anhydrous, calcium sulfate-dihydrate, calcium sulfate α-hemihydrate, calcium sulfate β-hemihydrate, and combinations thereof and a non-aqueous component having an aqueous replacement characteristic;
    inserting an expandable device into a bone;
    expanding said expandable device to create a cavity or space within the bone; and
    delivering said composition to the bone through a delivery device, wherein said non-aqueous component is replaced with aqueous body fluid, thereby hardening said composition to a crystalline state in vivo to provide a hardened bone substitute material.

17. A kit comprising:
    a percutaneous delivery device; and
    a composition consisting essentially of:
    a mineral component that hardens in an aqueous environment, wherein said mineral component is selected from the group consisting of calcium sulfate-anhydrous, calcium sulfate-dihydrate, calcium sulfate α-hemihydrate, calcium sulfate β-hemihydrate, and combinations thereof; and
    a non-aqueous component having an aqueous replacement characteristic that causes the composition to harden to a crystalline state in vivo when the non-aqueous component is replaced with aqueous body fluid.

18. A kit as in claim 17, further comprising instructions for use and setting forth a method comprising providing said composition; and delivering said composition to a bone, wherein said non-aqueous component is replaced with aqueous body fluid, thereby hardening said composition to provide a hardened bone substitute material in contact with the bone.

19. The kit of claim 17, wherein said percutaneous delivery device is selected from the group consisting of a bone filler device, a syringe, a needle, a cement gun, a reduced diameter bone filler device, and a modified tip to enable directional flow.

20. The kit of claim 19, further comprising a heating device or heat-pack.

21. A method comprising:
    providing the kit comprising: a percutaneous delivery device, and
    a composition consisting essentially of a mineral component that hardens in an aqueous environment, wherein said mineral component is selected from the group consisting of calcium sulfate-anhydrous, calcium sulfate-dihydrate, calcium sulfate α-hemihydrate, calcium sulfate β-hemihydrate, and combinations thereof; and
    a non-aqueous component having an aqueous replacement characteristic that causes the composition to harden to a crystalline state when the non-aqueous component is replaced with aqueous body fluid, wherein said composition is ready for use; and
    delivering said composition to a bone, wherein the non-aqueous component is replaced with aqueous body fluid, thereby hardening said composition to a crystalline state in vivo to provide a hardened bone substitute material in contact with the bone.

22. A bone cement composition consisting essentially of:
    a mineral component that hardens in an aqueous environment, wherein the mineral component consists essentially of calcium phosphate; and
    a non-aqueous component having an aqueous replacement characteristic that causes the composition to harden to a crystalline state in vivo when the non-aqueous component is replaced with aqueous body fluid, wherein the non-aqueous component is polyethylene glycol (PEG).

23. A bone cement composition consisting essentially of:
    a mineral component that hardens in an aqueous environment, wherein the mineral component consists essentially of calcium aluminate; and
    a non-aqueous component having an aqueous replacement characteristic that causes the composition to harden to a crystalline state in vivo when the non-aqueous component is replaced with aqueous body fluid, wherein the non-aqueous component is polyethylene glycol (PEG).

* * * * *